United States Patent
Ettema

(10) Patent No.: US 6,538,012 B2
(45) Date of Patent: Mar. 25, 2003

(54) AMLODIPINE HEMIMALEATE

(75) Inventor: Gerrit J. B. Ettema, Nijmegen (NL)

(73) Assignee: Synthon BV, Nijmegen (NL)

(*) Notice: Subject to any disclaimer, the term of this patent is extended or adjusted under 35 U.S.C. 154(b) by 0 days.

(21) Appl. No.: 09/938,821

(22) Filed: Aug. 27, 2001

(65) Prior Publication Data

US 2002/0128297 A1 Sep. 12, 2002

Related U.S. Application Data

(63) Continuation-in-part of application No. 09/809,356, filed on Mar. 16, 2001, now abandoned.
(60) Provisional application No. 60/258,603, filed on Dec. 29, 2000.

(51) Int. Cl.[7] ............... C07D 211/86; A61K 31/455
(52) U.S. Cl. ......................... 514/356; 546/321
(58) Field of Search ............... 546/321; 514/356

(56) References Cited

U.S. PATENT DOCUMENTS

| | | | |
|---|---|---|---|
| 4,572,909 A | * | 2/1986 | Campbell et al. ........... 514/356 |
| 4,870,091 A | * | 9/1989 | Peglio et al. ................ 514/356 |
| 4,879,303 A | | 11/1989 | Davison et al. |
| 4,983,740 A | | 1/1991 | Peglion et al. |
| 5,155,120 A | | 10/1992 | Lazar et al. |
| 5,389,654 A | | 2/1995 | Furlan et al. |
| 5,438,145 A | | 8/1995 | Furlan et al. |
| 6,046,337 A | | 4/2000 | Bozsing et al. |

FOREIGN PATENT DOCUMENTS

| | | |
|---|---|---|
| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

CA 105:172250, Arrowsmith et al. 1986.*
CA 101:210998, 1984.*
Alker et al., "Long–acting dihydropyridine calcium antagonists. 9. Structure activity relationships around amlodipine", Eur J Med Chem (1991) 26, 907–913.
Amlodipine Besylate Monograph, Pharmeuropa vol. 10, No. 2, 197–198, Jun. 1998.
Faulkner et al, "Absorption of Amlodipine Unaffected by Food", Arzneim Forsch/Drug Res. 39 (11), No. 7, (1989).
McDaid and Deasy, "Formulation development of a transdermal drug delivery system for amlodipine base", International Journal of Pharmaceutics 133 (1996) 71–83.
Arrowsmith et al., "Long–Acting Dihydropyridine Calcium Antagonists. 1. 2–Alkoxymethyl Derivatives Incorporating Basic Substituents", J. Med. Chem. American Chemical Society, 1986, 29, 1696–1702.
FDA FOIA Material on Amlodipine Besylate, NDA No. 19–787, "Review of an Original NDA", Oct. 10, 1990.

* cited by examiner

Primary Examiner—Jane Fan
(74) Attorney, Agent, or Firm—Fleshner & Kim, LLP

(57) ABSTRACT

Amlodipine hemimaleate is useful as a calcium channel blocker and can be used to treat or prevent angina or hypertension.

14 Claims, 2 Drawing Sheets

AMLODIPINE HEMIMALEATE

This application is a continuation-in-part application under 35 U.S.C. §120 of prior U.S. patent application Ser. No. 09/809,356, filed Mar. 16, 2001, now abandoned the entire contents of which are incorporated herein by reference. Further, this application claims the benefit of priority under 35 U.S.C. §119(e) from U.S. provisional patent application Ser. No. 60/258,603, filed Dec. 29, 2000, the entire contents of which are incorporated herein by reference.

BACKGROUND OF THE INVENTION

1. Field of the Invention

The present invention relates to a novel compound, to processes for preparing it and to its use in treating medical disorders. In particular the present invention relates to a novel acid addition salt of amlodipine.

2. Description of the Related Arts

Pharmaceutical products with antianginal and antihypertensive properties are described in U.S. Pat. Nos. 4,572,909 and 4,879,303. An especially important compound among those disclosed is amlodipine, ±2-[(2-aminoethoxy)methyl]-4-(2-chlorophenyl)-1,4-dihydro-6-methyl-3,5-pyridinedicarboxylic acid 3-ethyl 5-methyl ester. Amlodipine has the following structural formula.

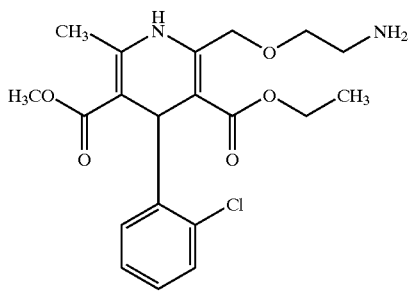

This compound is used for the preparation of a medicament having calcium channel blocking activity, useful in the management of the hypertension and angina pectoris. Particularly useful forms of amlodipine for use in human medicine are maleate and benzenesulfonate salts thereof. Examples 9, 11, 12 and 22 of U.S. Pat. No. 4,572,909 as well as J. Med. Chem. 29,1698(1986) disclose the preparation of amlodipine maleate (in 1:1 molar ratio) by dissolving a reaction mixture containing in situ prepared raw amlodipine base in ethylacetate or in ethanol and adding solid maleic acid while the maleate salt of amlodipine precipitates. The salt is then isolated by filtration and recrystallized from ethyl acetate or from acetone/ethyl acetate 1:1. The prior art disclosure of amlodipine maleate has thus been of a compound having a 1:1 molar ratio between amlodipine and maleic acid. This compound should be more precisely called amlodipine hydrogenmaleate.

SUMMARY OF THE INVENTION

The present invention relates to the discovery of a novel salt of amlodipine useful for the preparation of medicaments containing amlodipine and being a suitable equivalent to the marketed amlodipine benzene sulfonate. Specifically, the present invention relates to amlodipine hemimaleate of formula (1)

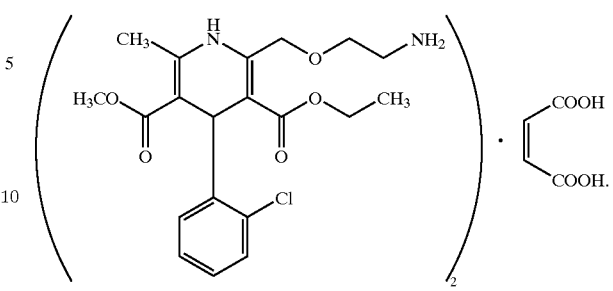

Another aspect of the present invention relates to a process that comprises contacting amlodipine free base or a salt thereof with maleic acid or its ammonium salt in the presence of a solvent to form amlodipine hemimaleate.

A further aspect of the present invention relates to a method for treating, or preventing angina or hypertension which comprises administering to a patient in need thereof an effective amount of an amlodipine hemimaleate as well as to a pharmaceutical composition for use in the treatment and/or prevention of angina or hypertension comprising an effective amount of amlodipine hemimaleate together with a pharmaceutically acceptable excipient.

DETAILED DESCRIPTION OF THE INVENTION

Figure 1:
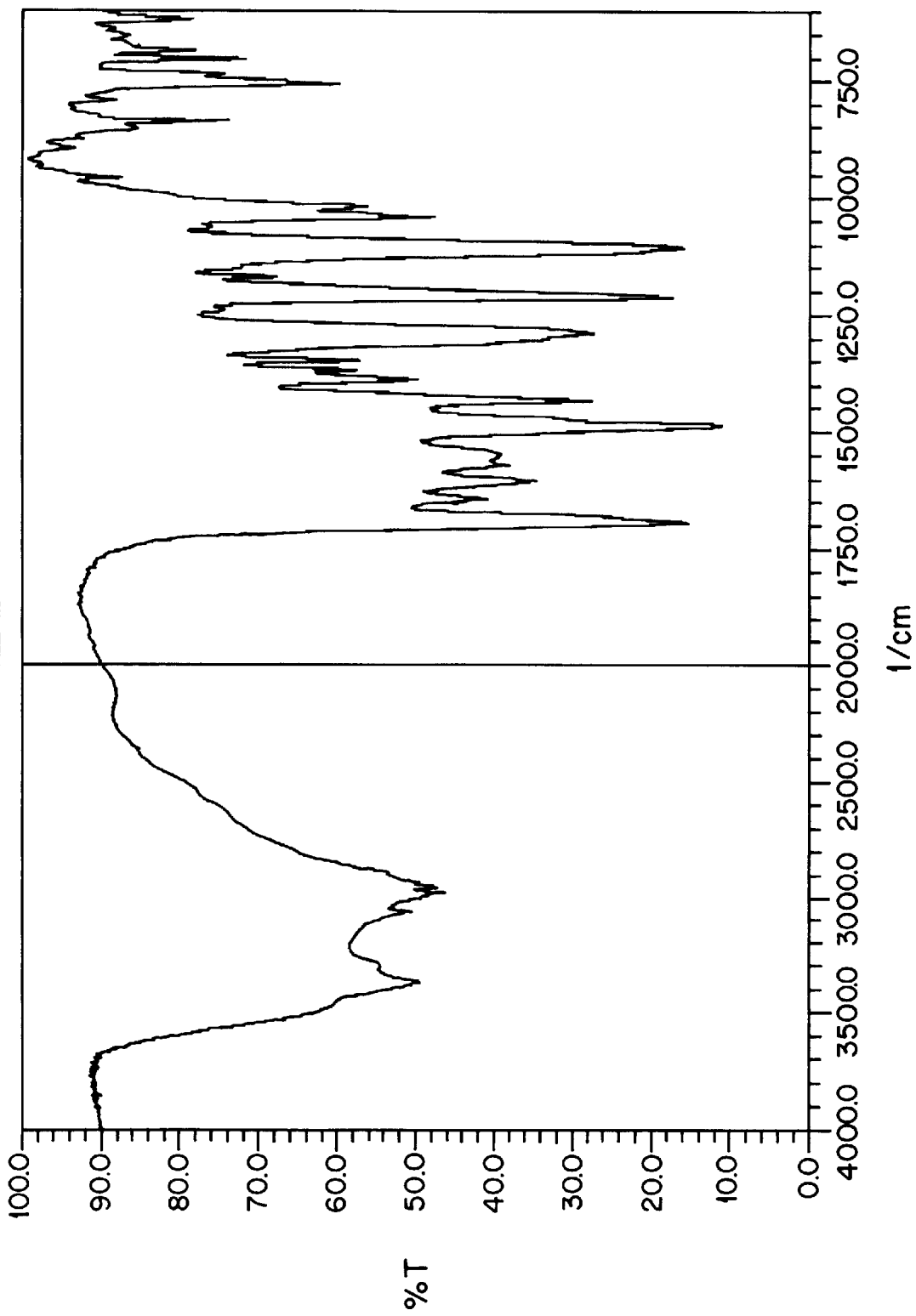
FIG. 1 is an IR spectrum of the material of Example 1.

The present invention is based on the discovery of a novel form of a maleate salt of amlodipine, namely amlodipine hemimaleate. A hemimaleate is characterised by essentially a 2:1 molar ratio between amlodipine and maleic acid. The compound of formula (1) is useful for the treatment of various cardiovascular disorders for example hypertension and angina.

The compound of formula (1) has a chiral centre on the 1,4-dihydropyridine ring of the amlodipine moiety, so it may exist in two optically active forms. The forms may be separated by crystallisation or chromatography of the free base, optionally as a salt with an optically active acid, and converted to the corresponding hemimaleate salt. The individual isomers, and mixtures thereof, of the compound of formula (1) are all within the scope of the singular term "amlodipine hemimaleate."

The present invention also provides a method for the preparation of the compound of formula (1), which comprises contacting amlodipine or a salt thereof with maleic acid to form amlodipine hemimaleate. Preferably, the amlodipine hemimaleate is precipitated from the solvent after the contacting step. The precipitation may be spontaneous at the temperature of mixing but it may also be facilitated by cooling the obtained solution, reducing the volume of the solution or by adding a contrasolvent, i.e. a liquid miscible with the solvent in which the amlodipine hemimaleate is less soluble. In one embodiment, two molar equivalents of amlodipine or a salt thereof are mixed with one equivalent of maleic acid or ammonium salt thereof in a suitable solvent, followed by precipitation of the amlodipine hemimaleate compound from the solvent. The temperature may vary from the melting point of the solvent, more typically from room temperature, up to the boiling point temperature of the solvent.

Amlodipine hemimaleate may however be formed when one equivalent of amlodipine or salt thereof is contacted with one equivalent of maleic acid; e.g. by dissolving 1:1 molar amounts of amlodipine base and maleic acid in very diluted aqueous environment (at least 200 ml water per 1 gram of amlodipine) at room temperature, whereby amlodipine hemimaleate spontaneously crystallizes after a certain latent period.

Amlodipine free base may be prepared according to the procedures generally outlined in U.S. Pat. No. 4,572,909. Another useful synthesis scheme for making amlodipine or salts thereof in good yields and purity via a phthalimidoamlodipine intermediate is described in commonly-owned provisional application Ser. No. 60/258,613, filed Dec. 29, 2000, the entire contents of which are incorporated herein by reference, and in commonly-owned co-pending U.S. patent application Ser. No. 09/809,351, filed on Mar. 16, 2001 and entitled "Process for Making Amlodipine, Derivatives Thereof, and Precursors Therefor," the entire contents of which are incorporated herein by reference. Maleic acid is commercially available.

Suitable solvents include water, an alcohol such as methanol or ethanol, a ketone such as acetone or methyl isobutyl ketone, an ester such as ethylacetate, an ether such as diethylether or tetrahydrofuran, a nitrile such as acetonitrile, a dipolar aprotic solvent such as dimethylsulfoxide or dimethylformamide, a hydrocarbon such as hexane or toluene and mixtures thereof.

In order to avoid the formation of certain impurities during the salt forming reaction, it may be desirable that the amlodipine and maleic acid are combined under acidic conditions as is more fully described in commonly-owned provisional application Ser. No. 60/258,612 filed Dec. 29, 2000, the entire contents of which are incorporated herein by reference, and in commonly owned co-pending U.S. patent application Ser. No. 09/809,343, filed on Mar. 16, 2001, and entitled "Process for Making Amlodipine Maleate," the entire contents of which are incorporated herein by reference.

The precipitated amlodipine hemimaleate may be isolated in a solid state by conventional methods such as filtration or centrifugation, optionally followed by washing and/or drying and may be purified by crystallization, for example at elevated temperature in an appropriate solvent, for example water, an alcohol such as methanol, or a ketone such as acetone. Such methods allow for the production of the compound in a crystalline state.

The amlodipine hemimaleate may also be obtained in an amorphous form, e.g. by freeze drying a solution thereof formed with a suitable solvent, e.g. in water. Such amorphous forms may be advantageous in comparison with the crystalline form as it may be obtained in a finely powdered form with good solubility properties.

Amlodipine hemimaleate may exist in a solvent-free form or it may be isolated as a hydrate or a solvate. After conventional isolation of a product obtained by crystallization or precipitation of amlodipine hemimaleate from an aqueous solution, i.e. after filtration, washing and drying in vacuo at ambient temperature, a hydrate of amlodipine hemimaleate is normally obtained. The product contains various amounts of water (up to 7%) and after prolonged drying in vacuo under slightly elevated temperature the amount of water reduces to the water content of approx. 1.9–2.0% corresponding to a monohydrate. On the other hand, after subjecting an anhydrous amlodipine hemimaleate to prolonged standing under increased humidity, hydrates comprising 2.5, 4 and 5 molar equivalents of water may be isolated. The amlodipine hemimaleate hydrates, especially the monohydrate, form a particular aspect of the invention and all are embraced by the above formula (1) as well as by the singular term "amlodipine hemimaleate."

Under drying at elevated temperatures, the bound water from a hydrate may be removed upon formation of an anhydrate. The anhydrate form of amlodipine hemimaleate is essentially metastable (hygroscopic) and, under ambient humidity and particularly at elevated humidity, slowly absorbs water and turns to a hydrated form. The dehydration and rehydration step may be advantageously used for improving/manipulating crystal size of the amlodipine hemimaleate hydrate. This is useful for practical applications of the hemimaleate in pharmaceutical dosage forms such as tablets or capsules where particle size of the active compound can have importance.

A methanol solvate of amlodipine hemimaleate can be prepared by precipitation of amlodipine hemimaleate from a methanolic solution, filtering and drying of the obtained solid in vacuo at ambient temperature. The methanol solvate contains approx. 6% of methanol, though the amount of bound methanol may vary. Prolonged drying in vacuo under elevated temperature yields an unsolvated amlodipine hemimaleate identical with the anhydrate described above.

It is not excluded that amlodipine hemimaleate forms solvates also with other solvents useful in its preparation or purification; such solvates are also within the scope of the invention.

Amlodipine hemimaleate can be characterised by a series of physical characteristics. It exhibits an IR spectrum clearly distinguishable from that of amlodipine maleate. If obtained in hydrated or solvated form, it has no defined melting point; DSC and TGA analysis indicates that it melts together with liberation of the bound solvent in a range of about 85–100° C.

The structure and amlodipine/maleic acid ratio of the product can be proven by measuring NMR spectrum under comparison with amlodipine maleate prepared by a method of the prior art.

Amlodipine hemimaleate is convertible to amlodipine in vivo and thus it basically shares the pharmaceutical activity of amlodipine. Accordingly, amlodipine hemimaleate is a useful calcium channel blocker and thus can be used to treat any cardiac condition that would be benefited by administration of a calcium channel blocker. In particular, the amlodipine hemimaleate can be used to treat or prevent hypertension or angina by administering an effective amount to a patient in need thereof. The specific form of angina is not particularly limited and specifically includes chronic stable angina pectoris and vasospastic angina (Prinzmetal's angina). Similarly, congestive heart failure can also be treated. The compound can be administered by any suitable route including orally or parenterally. The "patients" intended to be treated include human and non-human animals especially humans and non-human mammals.

The compound is usually administered as part of a pharmaceutical composition. Accordingly, a further aspect of the invention is a pharmaceutical composition for treating or preventing hypertension or angina that comprises an effective amount of amlodipine hemimaleate and a pharmaceutically acceptable excipient. Excipients include any inert or non-active material used in making a pharmaceutical dosage form. For example, tablet excipients include, but are not limited to, calcium phosphate, cellulose, starch or lactose. Capsules such as those made of gelatin, may contain or carry amlodipine hemimaleate alone or in admixture with other excipients. Liquid dosage forms are also included such as oral liquids in the form of liquors or suspensions, as well as injectable solutions. The pharmaceutical composition may be formulated for transdermal administration in the form of a patch. All of the above described pharmaceutical compositions may optionally contain one or more of each of the following excipients: carriers, diluents, colorants, flavoring agents, lubricants, solubilizing agents, disintegrants, binders and preservatives.

The pharmaceutical composition is normally provided in a unit dose. A unit dose is typically administered once or twice daily, more typically once daily. In the case of a transdermal patch, the unit dose (one patch) is generally applied at least once a month, more commonly at least once a bi-week, and typically once a week. An effective amount of amlodipine hemimaleate in a unit dose for treating or preventing hypertension or angina is generally within the range of 1 to 100 mg, typically 1 to 50 mg, more typically 1 to 20 mg. In solid oral dosage forms (tablets, capsules, etc.), the pharmaceutical composition typically contains about 1, 2.5, 5.0, or 10 mg of the amlodipine hemimaleate. For simplicity, all amounts refer to the corresponding amount of amlodipine free base provided to the composition. The usual initial human oral dose of amlodipine for both hypertension and angina is 5 mg once daily with a maximum dose of 10 mg once daily. Small, fragile, or elderly individuals, or patient with hepatic insufficiency may be started at 2.5 mg once daily and this dose may be used when adding amlodipine to other antihypertensive therapy. Specific examples of pharmaceutical compositions include those described in EP 244944 wherein amlodipine hemimaleate is used as the active ingredient.

Preferred pharmaceutical compositions will have a pH within the range of from about 5.5 to 7.0, when measured as a 20 wt % aqueous slurry as is described in more detail in commonly-owned co-pending U.S. patent application Ser. No. 09/809,346, filed on Mar. 16, 2001 and entitled "Pharmaceutical Compositions Comprising Amlodipine Maleate," the entire contents of which are incorporated herein by reference. These compositions generally provide good or improved stability.

All of the pharmaceutical compositions described above can be made by known methods and techniques. For example, the tablets can be made by dry granulation/direct compression or by a classical wet granulation method. Typically, tablets are made by blending, filling and compressing into tablets. The blending step may comprise a wet granulation or dry granulation. Similarly, capsules can be made by blending the ingredients and filling the capsule.

The following Examples illustrate the invention.

Example 1

Amlodipine Hemimaleate 50 g of Amlodipine free base and 7.1 g of maleic acid are added to 1250 ml of water at 50° C. The mixture is heated to 80° C. and stirred for 10 minutes. The resulting suspension is allowed to cool to room temperature and stirred at room temperature for 10 hours. A solid is formed and filtered off, washed with 2×50 ml of water and dried in a vacuum oven at 30° C.

Yield: 55.7 g (98% yield calculated on maleic acid)

Mp: 89.7° C.–94.7° C. (5° C./min) uncorrected

Mass Spectrum: FAB+:933.2

NMR spectrum:

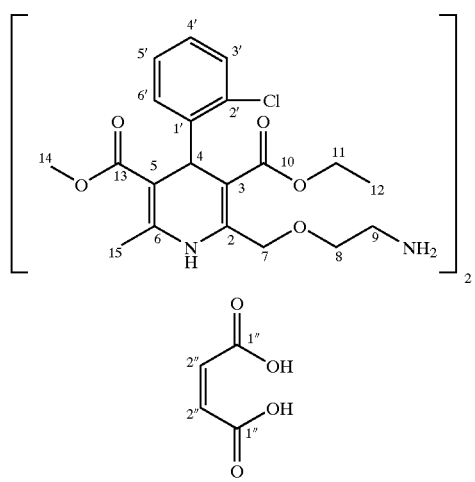

The $^1$H-NMR spectrum is measured at 303.2 K on a Bruker Avance-400 in deuterated dimethylsulfoxide at 400 MHz.

| δ | assignment |
|---|---|
| 1.13 | (t, 3H, $J_{11,12}$ = 7.0 Hz, H-12); |
| 2.33 | (s, 3H, H-15); |
| 2.95 | (bdd, 2H, H-9); |
| 3.53 | (s, 3H, H-14); |
| 3.59 | (bt, 2H, H-8); |
| 4.00 | (m, 2H, H-11); |
| 4.65 | (ABq, 2H, H-7); |
| 5.34 | (s, 1H, H-4); |
| 6.07 | (s, 1H, H-2"); |
| 7.15 | (dt, 1H, $J_{3',4'}$ = $J_{4',5'}$ = 7.8 Hz, $J_{4',6'}$ = 1.5 Hz, H-4'); |
| 7.25 | (bt, 1H, H-5'); |
| 7.28 | (dd, 1H, $J_{3',4'}$ = 7.8 Hz, $J_{3',5'}$ = 1.0 Hz, H-3'); |
| 7.37 | (dd, 1H, $J_{5',6'}$ = 7.6 Hz, $J_{4',6'}$ = 1.5 Hz, H-6'); |

$^{13}$C-NMR spectrum:

The $^{13}$C-NMR spectrum is measured at 303.2 K on a Bruker Avance-400 in deuterated dimethylsulfoxide at 100.6 MHz.

| δ | assignment |
|---|---|
| 13.97 | (C-12); |
| 18.07 | (C-15); |
| 36.76 | (C-4); |
| 39.58 | (C-9); |
| 50.37 | (C-14); |
| 59.23 | (C-11); |
| 66.59 | (C-7); |
| 69.52 | (C-8); |
| 101.85, 101.88 | (C-3, C-5); |
| 127.27 | (C-5'); |
| 127.65 | (C-4'); |
| 128.90 | (C-3'); |
| 130.92 | (C-6'); |
| 131.10 | (C-2'); |
| 136.01 | (2xC-2"); |
| 145.16, 145.22 | (C-2, C-6); |
| 145.72 | (C-1'); |
| 166.25 | (C-10); |
| 167.10, 167.21 | (2xC-1", C13). |

IR spectrum (KBr): See FIG. 1.

Example 2

Amlodipine Hemimaleate Monohydrate 2 g of amlodipine is added to a solution of 284 mg of maleic acid in 50 ml of water. The suspension is heated to 80° C. in 10 minutes to almost complete dissolution. The mixture is allowed to cool to room temperature. After 1 night stirring at room temperature the solid is filtered off and dried in a vacuum oven at 30° C. for 2 hours.

Water content (TGA): 2.9% water;

After prolonged drying for 2 days at 30 C in vacuo, the content of water decreased to 2.0%.

DSC: melting endotherm 83.1–92.1° C.

Figure 2:
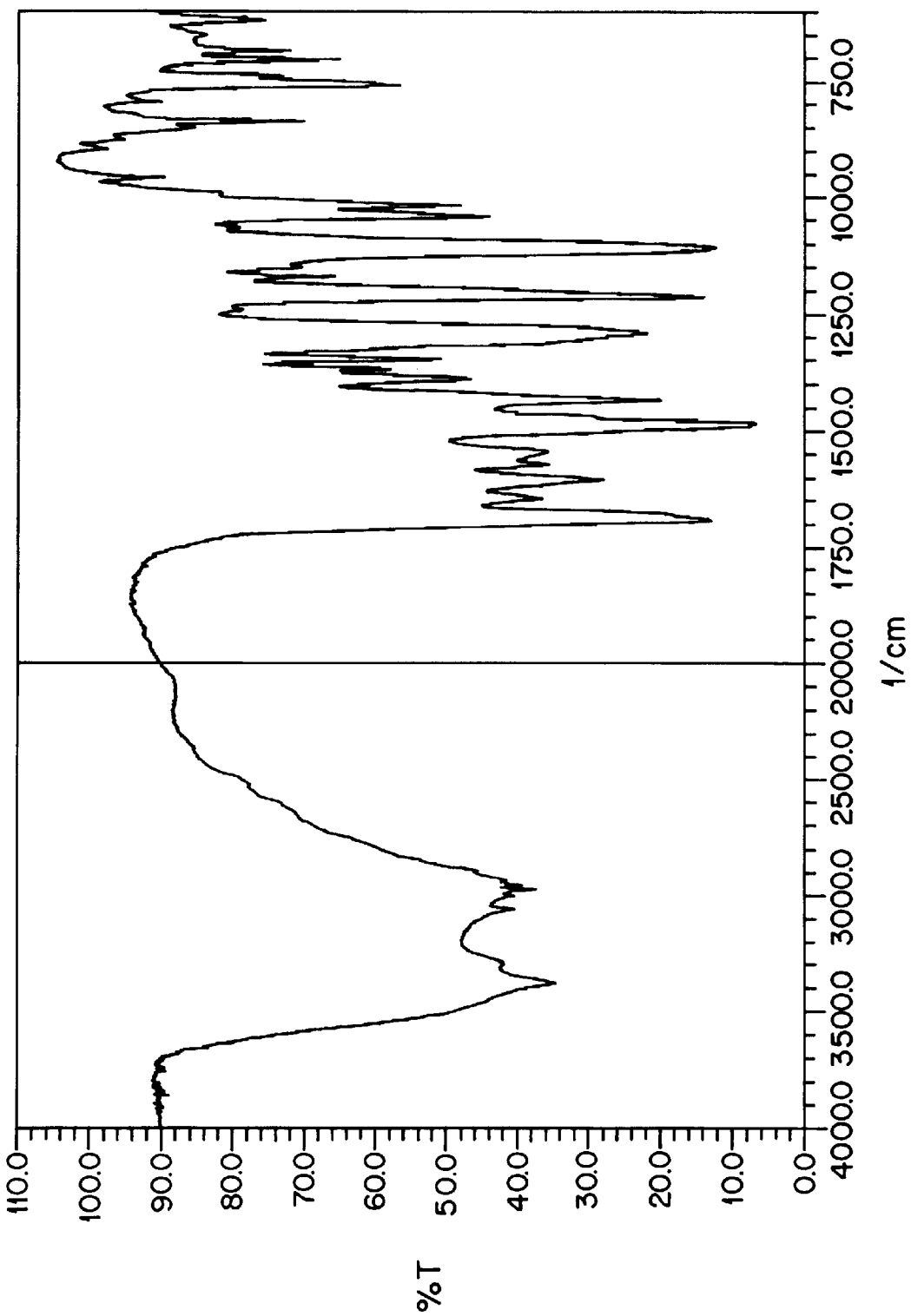
FIG. 2 is an IR spectrum of the material of Example 2.

IR spectrum: see FIG. 2.

Example 3

Amlodipine Hemimaleate Hydrate 285 mg of maleic acid is dissolved in 500 ml of water. The mixture is heated on a water bath to 80° C. and 2 g of amlodipine was added. The mixture is stirred for 15 minutes and the resulting suspension is filtered. The filtrate is allowed to cool to room temperature. A solid is formed and filtered off. The solid looks like small shiny plates (crystals). Dried in a vacuum oven at 25° C. for 1 night.

DSC: melting endotherm 93.9–100.0° C.

TGA: water content 3.1%.

Purity (HPLC) 98.9%.

Example 4

Amlodipine Hemimaleate—Preparation from 1:1 Molar Mixture 0.57 g of maleic acid is dissolved in 1000 ml of water. While stirring, 2 g of amlodipine (molar equivalent) is added. After standing in the dark at ambient temperature for 2 days, the solid is filtered off and dried in a vacuum oven at 30° C.

DSC: melting endotherm 76.4–88.8° C.

Purity (HPLC): 99+%.

Example 5

Amlodipine Hemimaleate Hydrate—Preparation from 1:1 Molar Mixture

To a solution of 0.57 g of maleic acid in 500 ml of water, 2 g of amlodipine is added. The amlodipine dissolves and a new solid is formed. After 2 days of standing at ambient temperature in the dark, the suspension is decanted. The wet solid is dried under vacuum at 30° C. for 2 hours.

TGA: melting endotherm 92.0–100.9° C., water 6.5%.

Purity (HPLC): 99+%.

Example 6

Amlodipine Hemimaleate Methanol Solvate 2 g of amlodipine base is dissolved in 10 ml of methanol. 285 mg of maleic acid is dissolved in 10 ml of methanol. This solution is added to the methanolic solution of amlodipine and set aside at −20° C. After 5 days the formed solid is filtered off and dried under vacuum at ambient temperature.

Methanol content: 6.5%.

DSC: melting endotherm 92.5–96.5° C.

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

I claim:

1. Amlodipine hemimaleate of formula (1)

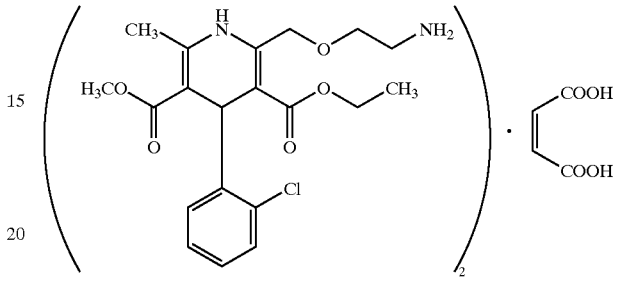

having an $^1$H-NMR spectrum including the following δ (ppm) peak values: 1.13 (t, 3H); 2.33 (s, 3H); 2.95 (bdd, 2H); 3.53 (s, 3H); 3.59 (bt, 2H); 4.00 (m, 2H); 4.65 (ABq, 2H); 5.34 (s, 1H); 6.07 (s, 1H); 7.15 (dt, 1H); 7.25 (bt, 1H); 7.28 (dd, 1H); and 7.37 (dd, 1H); when measured at 303.2 K in deuterated dimethylsulfoxide at 400 MHz; and having a $^{13}$C-NMR spectrum including the following δ (ppm) peak values: 13.97; 18.07; 36.76; 39.58; 50.37; 59.23; 66.59; 69.52; 101.85,101.88; 127.27; 127.65; 128.90; 130.92; 131.10; 136.01; 145.16,145.22; 145.72; 166.25; 167.10, and 167.21; when measured at 303.2 K in deuterated dimethylsulfoxide at 100.6 MHz.

2. Amlodipine hemimaleate of claim 1 in a crystalline state.

3. Amlodipine hemimaleate of claim 1, wherein said hemimaleate is amlodipine hemimaleate monohydrate.

4. A process, which comprises contacting amlodipine free base or a salt thereof with maleic acid or its ammonium salt in the presence of a solvent to form amlodipine hemimaleate of claim 1.

5. The process according to claim 4, wherein the solvent is selected from the group consisting of water, an alcohol, a ketone, an ester, an ether, a nitrile, a dipolar aprotic solvent, a hydrocarbon, and mixtures thereof.

6. The process according to claim 5, wherein said solvent is selected from the group consisting of water, methanol, ethanol, acetone, methyl isobutyl ketone, ethylacetate, diethylether, tetrahydrofuran, acetonitrile, dimethylsulfoxide, dimethylformamide, hexane, toluene and mixtures thereof.

7. The process according to claim 4, further comprising precipitating said amlodipine hemimaleate from the solution.

8. The process according to claim 7, wherein said precipitation is spontaneous or is induced by decreasing the temperature, decreasing the volume or adding a contrasolvent.

9. A method for treating or preventing angina or hypertension which comprises administering to a patient in need thereof an effective amount of a compound according to claim 1.

10. The method according to claim 9, wherein said compound is amlodipine hemimaleate monohydrate.

11. A pharmaceutical composition for use in the treatment and/or prevention of angina or hypertension comprising an effective amount of a compound according to claim 1 and a pharmaceutically acceptable excipient.

12. The pharmaceutical composition according to claim 11, wherein said composition is a unit dosage form for oral administration and said effective amount is within the range of 1–20 mg, based on the weight of the amlodipine free base.

13. The pharmaceutical composition according to claim 12, wherein said unit dosage form is a tablet or capsule form.

14. The pharmaceutical composition according to claim 13, wherein said effective amount is 2.5, 5 or 10 mg, based on the weight of the amlodipine free base.

* * * * *